United States Patent
Granov et al.

(10) Patent No.: US 10,262,760 B2
(45) Date of Patent: Apr. 16, 2019

(54) SYSTEM AND METHOD OF INTERACTIVE NAVIGATION OF SUBJECT'S TREATMENT

(71) Applicant: New N.I. Medical (2011) LTD, Petah Tikva (IL)

(72) Inventors: Igor Granov, Raanana (IL); Aviad Livneh, Savion (IL)

(73) Assignee: New N.I. Medical (2011) LTD, Petah Tikva (IL)

( * ) Notice: Subject to any disclaimer, the term of this patent is extended or adjusted under 35 U.S.C. 154(b) by 686 days.

(21) Appl. No.: 14/857,891

(22) Filed: Sep. 18, 2015

(65) Prior Publication Data

US 2016/0085930 A1  Mar. 24, 2016
US 2017/0039333 A9  Feb. 9, 2017

(30) Foreign Application Priority Data

Sep. 23, 2014  (IL) .......................................... 234823

(51) Int. Cl.
*G16H 50/20* (2018.01)
*G16H 40/63* (2018.01)
(Continued)

(52) U.S. Cl.
CPC ............. *G16H 50/20* (2018.01); *A61B 5/021* (2013.01); *A61B 5/024* (2013.01); *A61B 5/029* (2013.01);
(Continued)

(58) Field of Classification Search
CPC ... A61B 5/029; A61B 5/02028; A61B 5/0205; G06F 19/26; G16H 50/20; G16H 50/30
(Continued)

(56) References Cited

U.S. PATENT DOCUMENTS

2005/0043965 A1* 2/2005 Heller .................. G06F 19/326
 705/2
2012/0130697 A1* 5/2012 Woodford ............ A61B 5/0205
 703/11
(Continued)

FOREIGN PATENT DOCUMENTS

WO  9637859 A1  11/1996

OTHER PUBLICATIONS

NIMedical, Understanding of NICaS Parameters, Jun. 2, 2011, www.ni-medical.com/technology/nicas-parameters/, pp. 1-3 (Year: 2011).*

*Primary Examiner* — Joy Chng
(74) *Attorney, Agent, or Firm* — Arent Fox LLP; Michael Fainberg

(57) ABSTRACT

System and method for monitoring a subject's condition. The system comprises a data input utility for receiving medical data indicative of a first condition of a subject; a communication utility for obtaining reference data comprising at least two predefined multi-dimensional functions and a multi-parameter space within said functions corresponding to a normal condition of a subject; a processing utility for processing said medical data of a subject by identifying a plurality of individual medical parameters describing said at least two predefined multi-dimensional functions, analyzing the identified plurality of individual parameters and determining a relation between the parameters and said multi-parameter space, for determining a treatment plan for navigating the subject from said first condition to a second subject condition in which values of said plurality of medical parameters define a parametric space matching the multi-parameter space of the normal condition; and an output utility for outputting said treatment plan.

24 Claims, 8 Drawing Sheets

(51) Int. Cl.
- *G16H 10/60* (2018.01)
- *G06F 19/00* (2018.01)
- *A61B 5/107* (2006.01)
- *A61B 5/029* (2006.01)
- *A61B 5/024* (2006.01)
- *A61B 5/021* (2006.01)

(52) U.S. Cl.
CPC .............. *A61B 5/107* (2013.01); *G06F 19/00* (2013.01); *G16H 10/60* (2018.01); *G16H 40/63* (2018.01)

(58) Field of Classification Search
USPC .......................................................... 705/2–3
See application file for complete search history.

(56) References Cited

U.S. PATENT DOCUMENTS

| | | | | |
|---|---|---|---|---|
| 2013/0310691 A1* | 11/2013 | Furman | ..................... | A61B 8/06 600/447 |
| 2014/0276034 A1* | 9/2014 | Eggers | ................. | A61B 5/0275 600/431 |
| 2014/0277240 A1* | 9/2014 | Maskara | .............. | A61N 1/3684 607/18 |

* cited by examiner

SYSTEM AND METHOD OF INTERACTIVE NAVIGATION OF SUBJECT'S TREATMENT

TECHNOLOGICAL FIELD

The present invention relates to a medical system and method for medical condition management in living beings. In particular, the invention provides the ability to navigate a subject from an unstable or undesirable hemodynamic state to a stable or desired hemodynamic state.

BACKGROUND

Hemodynamic management and evaluation of patient's hemodynamic status is commonly implemented in the general and cardiac intensive care units (ICU and ICCU), during patient transport, intermediate care units, during anesthesia and post anesthesia care units (PACU). Having online and real time information about values of important parameters, such as cardiac output, stroke volume, heart rate and arterial pressure can significantly help the physicians save lives by monitoring and treating critical conditions effectively.

Hypotension, for example, is very common in critically ill patients, and intravascular volume is often difficult to evaluate. Prolonged hypotension and suboptimal internal organ perfusion may lead to tissue ischemia, multi-organ failure, and poor outcome. Thus, urgent response is required.

While clinical examination is important, it may not be sufficient, quick or accurate enough for evaluating and promptly treating critically ill patients admitted to the ICU or other relevant units.

US 2012/0130697 discloses a method for determining haemodynamic performance in a human or animal subject comprises receiving at a processor data representing haemodynamic variables measured from the subject over time. The haemodynamic variables comprise at least two of Systemic Perfusion Pressure (SPP), Systemic Vascular Resistance (SVR), Cardiac Output (CO), Heart Rate (HR) and Stroke Volume (SV). The data are processed to produce a display signal for causing a display device to present a visual mapping relating the haemodynamic variables according to the relationship SPP=CO×SVR and the visual mapping is displayed on a display device. The visual mapping may be corrected Heart Rate (HR) or include a second mapping which facilitates an adjustment to take account of HR.

WO 96/37859 discloses a method of attaining a preselected systemic hemodynamic state in a patient using a per-beat basis, such as for example paired values of MAP and SI, rather than a per-minute basis, such as MAP and CI. Also disclosed is a method of utilizing Hemodynamic Management Charts (HMCs) which permits the integration of data concerning systemic hemodynamic modulators and the systemic hemodynamic state, and which allows the identification of deviations in the levels of the hemodynamic modulators from normal levels. Also, a computer-based system is disclosed, the system measures hemodynamic parameters and implements at least one HMC into its software, thereby permitting identification of deviations in the levels of hemodynamic modulators from normal levels. Therapeutic corrections of the deviations in hemodynamic modulator levels, such as through pharmacologically active agents or volume expanders, based on the foundation and HMCs enables the clinician to establish and maintain a patient in the normal hemodynamic state and normal perfusion state.

SUMMARY

There is a need in the art to provide vital information about a condition of a subject, in particular hemodynamic health state of a human subject, and convey this information to practitioners in such a way to enable effective and as short as possible plan to stabilize the medical state of the subject, e.g. to suggest a treatment plan for aiding a subject to recover from critical illness.

The present invention relates to a novel monitoring system which receives, continuously or periodically, personal data measured by same or another system, and database data comprising normal or desired (as defined by the treating physician) values (boundaries) of parameters (variables) of plurality of functions; processes all or part of the personal data thereby acquiring personal medical parameter values corresponding to said plurality of functions, then analyzes the data of the personal medical parameters and the normal parameter values (forming a multi-parameter space in the functions) to obtain a relation thereof, thereby enabling to plan a treatment procedure for navigating the individual parameter values of all functions into normal or desired zones of said functions as defined by the normal values/boundaries.

The system outputs the treatment plan and the navigation as real time information to a user. The output data may be preferably graphically presented, and preferably together with the data of normal/desired condition, thereby clearly and conveniently illustrating the navigation route/treatment plan towards the desired result. The system may check the plan after the receipt of each new measured individual data and applies changes to the plan if necessary. The system may be configured to connect to another system which executes the plan, e.g., drug delivery systems that modulate the dose of the drug delivery according to hemodynamic input conveyed by the system. At each stage, the plan may be executed automatically or upon a user approval. The system enables a friendly and meaningful interface, which may direct a novice practitioner effectively and efficiently through the treatment stages. The system may also be programmed to provide simulations/predictions to an outcome of treatment plan(s) including one or more stages, thus helping the user (physician, operator) in the treatment planning procedure. The plurality of functions, the multi-parameter space of normal values and the personal medical parameters may be output by the system and presented on a device (a monitor or a speaker), giving the user visual or audible interaction.

According to the invention, in order to properly construct a treatment plan, e.g. in the form of an automatic closed loop drug delivery plan, for a patient requiring hemodynamic balance, the following conditions of the patient are to be concurrently analyzed: his/her total peripheral resistance index and cardiac power index as a function of cardiac output index and blood pressure, generally known as Cardiovascular Status, and his/her cardiac output index as a function of heart rate and stroke volume index, generally known as Cardiac Function.

The inventors have found that analyzing only one of the above functions is either not enough to decide about a definitive treatment plan or requires unnecessarily and time-consuming preliminary examinations and treatments (by drugs). These drawbacks become critical in intensive care settings (e.g. emergency rooms).

Both functions should be considered simultaneously and concurrent dual presentation of data relating to both functions is needed. More specifically, it might be that looking solely on the Cardiac Function (e.g., cardiac output index vs. heart rate and stroke volume index) provides practically no information or does not provide meaningful information about the condition of the peripheral blood flow, while data about this condition is important. For example, a patient might seem to require an inotropic drug (as his stroke volume is low), while a real treatment should be by vasodilating agent because of high Total Peripheral Resistance Index (TPRI), which cannot be identified solely from the Cardiac Function. On the other hand, analysis of the total peripheral resistance index and cardiac power index vs. cardiac output index and blood pressure alone does not allow taking into account the patient's heart rate distribution over the stroke volume, and thus will compromise the treatment. For example, a vasoconstricted patient might have either low heart rate and normal stroke volume, or low stroke volume and high heart rate, while having the same blood pressure and cardiac output index conditions.

The Cardiovascular Status and Cardiac Function are preferably represented graphically in order to allow the physician or other medical personnel a quick integrative understanding of the patient hemodynamic status and the nature and magnitude of change that needs to be done. The dual presentation of data regarding the two functions may include a normal or desired zone, i.e. a multi-parameter space of well defined boundaries, being the safe/desired zone in which a balanced subject is found and to which an ill subject should be brought to, as will be defined by the treating physicians. In particular, the authorized user (e.g. physician or other medical personnel) is allowed to redefine a zone in which an adequate hemodynamics is achieved for a specific subject. The subject's measured data is positioned on the graph with respect to the normal/predefined zone enabling navigating the subject from his current (measured) positions into the safe zones on both graphs of both functions.

Instead of or in addition to a physician (a human decision), a system (e.g. a computer hardware or software) may provide automatic recommended/proposed treatment plan based on the analysis of the two functions. The system may have a base data including stored data about the safe zones' predefined zones regarding each of the functions, and all known medical data regarding acceptable medications/treatments. The system receives individual data about the subject according to both functions and compares the individual data with the safe zones, then plans and calculates the minimal needed treatment steps to cause stabilization of the treated subject and moving him into each one of the safe zones.

The system may be configured as an off-line monitor, or as on-line monitor. In the latter case, a patient is monitored online, and his cardiovascular status and cardiac function are traced continuously until he enters the safe zones in both categories.

The system may comprise a memory utility (module) for permanently collecting data, said data may be used for updating the safe zone limits.

Thus, according to one broad aspect of the invention, there is provided a computerized system for use in monitoring a subject's condition, the system comprising:

a data input utility configured and operable for receiving medical data of a subject being indicative of a first subject condition, a communication utility configured and operable for accessing a database for obtaining therefrom reference data comprising at least two predefined multi-dimensional functions of medical parameters and a multi-parameter space within said functions corresponding to a normal condition of a subject;

a processing utility connected to the data input utility and to the communication utility, said processing utility being preprogrammed for processing said medical data of a subject utilizing said at least two predefined multi-dimensional functions, said processing comprising:

a parameter identifier configured and operable for identifying in said medical data a plurality of individual medical parameters describing said at least two predefined multi-dimensional functions, an analyzer configured and operable for analyzing the identified plurality of medical parameters and determining a relation between the plurality of individual medical parameters and said multi-parameter space, and utilizing said relation for determining a treatment plan for navigating the subject from said first condition to a second subject condition in which values of said plurality of medical parameters define a parametric space matching the multi-parameter space of the normal condition according to a predetermined degree of match, and an output utility for generating output data indicative of said treatment plan.

In some embodiments, the output utility is configured and operable for simultaneous presentation of said at least two multi-dimensional functions and said plurality of individual medical parameters within said multi-dimensional functions, thereby presenting said relation between the first condition of the subject and the second condition of the subject. This preferably includes graphical presentation.

In some embodiments, the medical data of a subject comprises two or more of the following: Heart Rate (HR), Blood Pressure (BP). Systolic Blood Pressure (SBP), Diastolic Blood Pressure (DBP), Body Surface Area (BSA), Stroke Volume (SV) and Cardiac Output (CO).

The plurality of identified parameters may comprise at least two of the following: Mean Arterial Pressure (MAP), Total Peripheral Resistance Index (TPRI), Cardiac Power Index (CPI), Cardiac Output (CO), Cardiac Index (CI), Stroke Volume (SV) and Stroke Index (SI).

In some embodiments, the identifier utility is configured for using the medical data and calculating therefrom at least some of said plurality of the parameters describing said at least two predefined multi-dimensional functions.

The at least two predefined multi-dimensional functions may include: a multi-dimensional function of MAP, SBP and DBP vs. CI, and TPRI and CPI as functions of MAP and CI, describing Cardiovascular Status of a subject; and a multi-dimensional function of SI vs. HR, and CI as a function of SI and HR, describing a Cardiac Function of a subject. The multi-parameter space of the normal condition may be defined by the following normal parameter values: $70<MAP<105$, $2.5<CI<4.0$, $0.45<CPI<0.85$, $1600<TPRI<3000$, $35<SI<65$, and $60<HR<90$.

In some embodiments, the processor utility is configured and operable for automatically generating instructions for implementation of the treatment plan.

The system may be also configured for receiving a user input and generating instructions for implementation of the treatment plan based on the user input.

The system may also include a memory utility for storing the medical data of a subject and the identified parameter values, and the multi-parameter space of the normal condition.

In some embodiments, the processor utility may be further configured and operable for updating the multi-parameter space of the normal condition based on said medical data of a subject.

According to another broad aspect of the invention, it provides a computerized method for use in monitoring a subject condition, the method comprising:

operating a data input utility of a computer for receiving medical data indicative of a first subject condition, accessing a database for obtaining therefrom reference data comprising at least two predefined multi-dimensional functions of medical parameters and a multi-parameter space within said functions corresponding to a normal condition of a subject;

processing and analyzing the medical data utilizing said at least two predefined multi-dimensional functions, said processing and analyzing comprising: identifying in said medical data a plurality of individual medical parameters describing said at least two predefined multi-dimensional functions, analyzing the identified plurality of individual medical parameters and determining a relation between the plurality of individual medical parameters and said multi-parameter space, and utilizing said relation for determining a treatment plan for navigating the subject from said first condition to a second subject condition in which values of said plurality of individual medical parameters define a parametric space matching the multi-parameter space of the normal condition according to a predetermined degree of match, and generating output data indicative of said treatment plan.

In all embodiments, the present invention utilizes a number of hemodynamic parameters, part of which have been mentioned above, to be used by the system or the physician, for diagnosis of the patient's hemodynamic state, and for planning the treatment to aid the patient reaching a balanced hemodynamic state. These parameters are identified in measured data, e.g. including the measured parameter(s) and/or calculated parameters(s) using one or more of the measured parameters. Thus, some of these parameters are measured while others are calculated. For the sake of clarity these parameters are described herein after, however it should be noted that the definition of these parameters is usually universal and is not limited to the invention.

Heart Rate (HR)

Heart rate represents the number of times the heart beats per minute. It is expressed in beats per minute (bpm). Heart rate is based upon the number of QRS complexes detected on an ECO signal. The normal adult range for resting heart rate is 60-90 bpm. Rates less than 60 bpm are termed "bradycardia" and rates above 90 bpm are termed "tachycardia".

Stroke Volume (SV), Stroke Index (SI)

Stroke volume is the amount of blood pumped by the left ventricle each beat. Stroke index is the stroke volume divided by the body surface area (BSA), to normalize it for body size.

There are three primary factors that determine stroke volume. These are preload, contractility, and afterload. Preload refers to the amount of blood in the ventricle at the end of diastolic filling, which is also known as "End Diastolic Volume". Myocardial contractility is determined by the intrinsic force-velocity relationship of the myocardial muscle fibers. The contractile state of the heart may be affected by neural and/or humoral (substances in the blood stream secreted by the body systems), or pharmacological agents. Afterload refers to the amount of resistance to blood flow in the arterial system. The overall resistance is determined by the diameter of the aortic valve, distensibility of the aorta, and degree of constriction/dilation of the arterial system. When other factors are held constant, the greater the resistance, the less volume will be ejected with each heartbeat.

There are generally three primary reasons that the SV may be low: hypovolemia (low blood volume, which results in low preload), left ventricular dysfunction (poor myocardial contractility), and high peripheral resistance. Consequently, changes in SV can be early indicators of changes in blood volume and myocardial contractility. Manipulation of peripheral resistance can be of high impact on SV, and lowering TPR may be an important tool in order to increase SV. On the other hand, for a patient in which TPR is very low (Septic shock) increasing the TPR might increase SV. In many patients there is a range of TPR in which a negative linear correlation exists between SV and TPR.

Cardiac Output (CO)/Cardiac Index (CI)

The amount of blood pumped by the heart in one minute is the cardiac output. It is the product of heart rate×stroke volume, and is expressed in absolute terms of liters/minute (l/min). To normalize for body size, cardiac output is divided by body surface area (BSA) and is named cardiac index.

One of the major factors which affect cardiac output is the metabolic rate of the body. Consequently, factors that affect the metabolic rate also affect the cardiac output. For example: age, posture, exercise, body temperature, body size and composition, diseases and gender.

Cardiac output is an extremely informative physiological parameter. Changes in cardiac output can provide a much earlier warning of significant changes in the body's function or metabolic needs than changes in blood pressure. For example, cardiac output may change as much as 30% before any changes are noted in blood pressure. This is due to reflex cardiovascular changes (vasoconstriction and vasodilation) that attempt to maintain a stable blood pressure.

While monitoring critically ill patients, the metabolic needs of these patients are much greater than healthy persons of the same size. Consequently, a cardiac index of 2.0-3.0 l/min/m$^2$ for a critically ill patient could be life-threatening, even though 2.5 l/min is usually considered within normal limits. In addition, a sudden reduction in a patient's cardiac output/index could be life-threatening.

Cardiac output may be increased by modifying any of the underlying parameters that affect the output. These include increasing heart rate, increasing stroke volume by increasing preload, contractility or decreasing afterload.

Cardiac Power Index (CPI)

Cardiac Power Index is considered to be an indicator of myocardial contractility (i.e., speed and strength of contraction). In other words, it is indicator of the heart's ability to generate enough force to pump blood into the arterial system. CPI has been shown to be a strong predictor of outcomes in heart failure patients, i.e., the lower the CPI, the worse the prognosis.

Total Peripheral Resistance (TPR)/Total Peripheral Resistance Index (TPRI)

Total peripheral resistance is the resistance to the flow of blood through the arterial system. This parameter is not directly measured, but is calculated by dividing Mean Arterial Pressure (MAP) by CO. TPRI, unlike SI and CI (which are divided by BSA to index them to body size), is derived by dividing MAP by CI.

TPR is a calculated parameter and is expressed in resistance units of "Hg/liters/minute" or in metric units of "dynes×sec/cm$^5$". The normal range is 770 to 1500 dynes×sec/cm$^5$, when expressed in metric units.

TPR is determined primarily by the amount of compliance of the aorta and the amount of constriction or dilation in the peripheral arterial system. Circulating blood volume and hematocrit will also contribute to TPR. Factors that increase TPR are hypovolemia, hypothermia, low cardiac output states, and vasoconstricting agents. Factors that produce a low TPR are: septic and hypovolemic shock, anemia, and vasodilator agents.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

Figure 1:
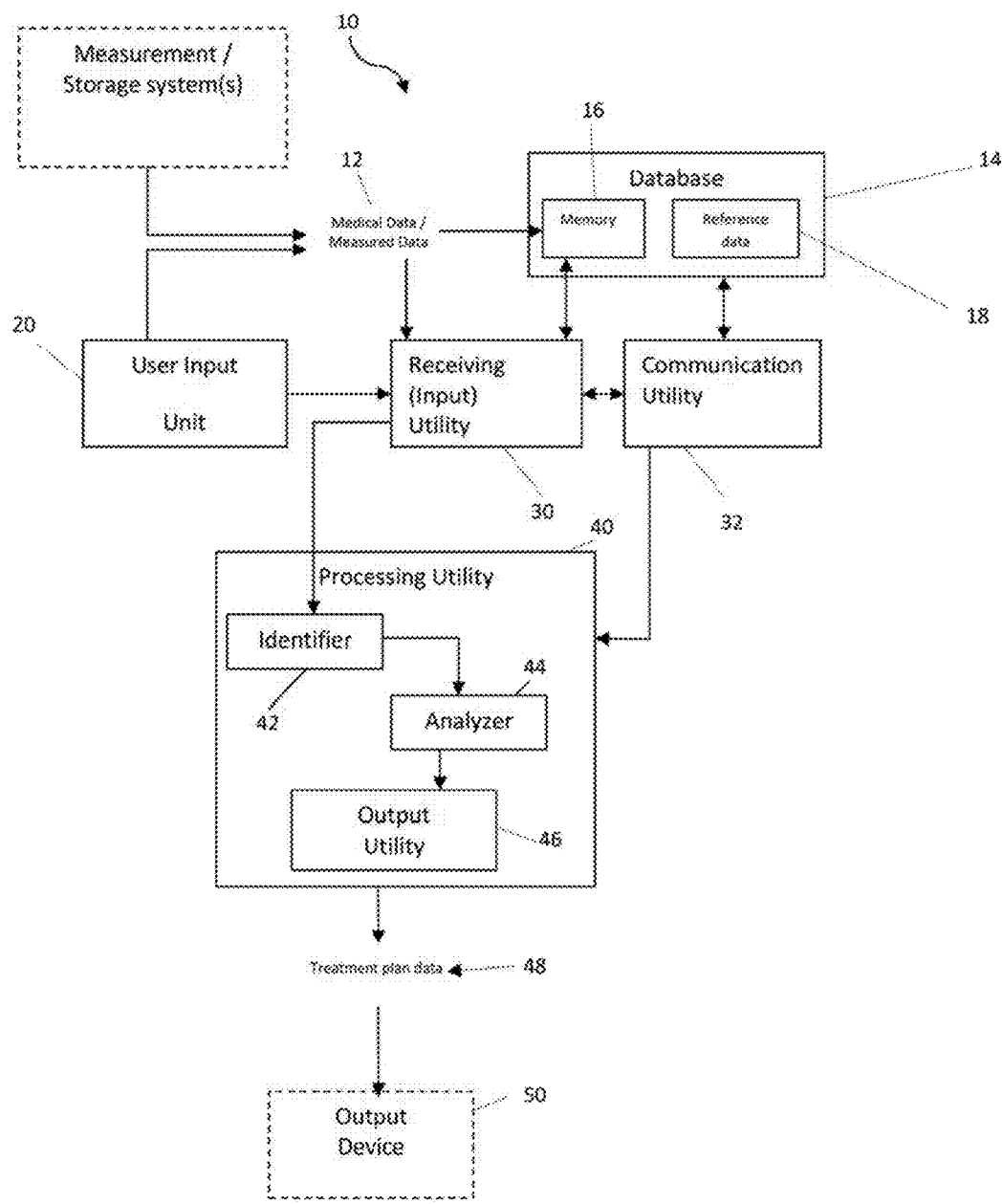
FIG. 1 shows an example of a system according to the present invention.

Reference is made to FIG. 1 illustrating one example of a system configured in accordance with the present invention. The system 10 is generally configured as a computerized system and includes a data receiving (input) utility 30, a communication utility 32, a processing utility 40, a user input unit 20 and a database utility 14. The system utilities may be physical units/entities and/or computer implemented software/hardware. For example, the system 10 may be a computer running a custom firmware or software.

The receiving utility 30 is connected to and receives data from the user input unit 20 and one or more measurement or storage devices (shown in dashed lines, not forming constructional part(s) of the system 10). The receiving utility 30 is also connected to and outputs data to the processing utility 40. The receiving utility 30 may operate in a continuous/periodic (automatic) mode or in on-demand (manual) mode for receiving medical data 12, either measured calculated or stored, and then delivering it to the processing utility 30. Additionally or alternatively, the medical data 12 may be sent directly or indirectly (through the receiving utility 30 and/or the communication utility 32) to the database utility 14 and stored there in a memory 16, to be then forwarded to the receiving utility 30 or processing utility 40 when needed. The individual medical data 12 may also be provided to the receiving utility 30 by a user via the user input unit 20 as shown in FIG. 1.

The database 14 may be a storage utility implemented in the system 10, or may be a cloud-based, remote server-based storage that can be accessed by the system via the communication utility 32. The database 14 stores data in different forms, including but not only, measured (raw) medical data, calculated (processed) medical data (parameters or variables of functions that will be presented by the system), collective database data (raw and/or calculated) in the form of reference data. The database may also maintain model data (mathematical formulations/algorithms) to be used for calculating the calculated individual or collective data from measured (raw) data, algorithms for calculations or processing of data, predefined parameter axis values (to be used at the displaying stage) and others. Some of these data, such as the mathematical formulations and algorithms, are to be used or executed by the processing utility 40. For example, shown in the figure is reference data 18 that may include data of predefined multi-dimensional functions, values of function parameters that constitute a multi-parameter space (e.g. based on collective data that was collected from large number of subjects), this multi-parameter space may define boundaries for safe/normal zone for each of the involved functions. The database including the multi-parameter space may be interactively updated upon usage and gathering of individual medical data 12. The stored data in the database may include data gathered from plurality of healthy users, e.g. regarding their hemodynamic status, such as parameter values of MAP, CI, CPI, TPRI, SI and HR. The database may store the boundaries of normal values (minimum and maximum) that form the multi-parameter space, in the involved functions, which defines safe zone(s).

The database 14 may also store reference data 18 about predefined solutions which may be used in a treatment plan according to the invention. The predefined solutions may be in the form of algorithms that the system 10 may output to the user as will be further described below.

The processing utility 40 may be a CPU, a SoC or other chip of the kind known in the art for execution of computation algorithms used in the invention. The processing utility 40 includes modules that perform different processing activities. In some embodiments, the modules include an identifier 42, an analyzer 44, and an output utility 46. The processing utility 40 receives the patient specific medical data (individual data) 12 (measured on-line or stored in the memory), and may also, if needed, perform calculations using the mathematical formulations, to identify, by the identifier 42, the individual medical parameters that describe the multi-parameter functions. The identification process may involve calculations done on the measured medical data in order to obtain the desired individual medical parameters. For instance, if the user (e.g. physician) is interested in displaying and/or analyzing the function of MAP vs. CI, there is a need to calculate CI from measured raw medical data, supplied by measurement devices or user input, which are HR, SV and BSA, as mentioned above.

The processing utility 40 also receives the values of the parameters forming the multi-parameter space from the reference data 18, analyzes both the individual medical parameters and the multi-parameter space in order to determine a relation between them, and uses this relation to output a treatment plan by utilizing predefined solutions that tell for each relation what the treatment step should be based on degree of desired predefined matching between the individual medical parameters and the multi-parameter space. A treatment plan will be generated by the output utility 46, aiming that the individual medical parameters of a subject be altered by the treatment in order to approach the region of the multi-space parameters.

The processing utility 40 may use received medical data 12 in order to update the normal (safe) function values of the multi-parameter space. The update may be an automatic procedure, based on predefined rules or according to a feedback from the user about specific individual medical parameter values.

Figures 2, 3:
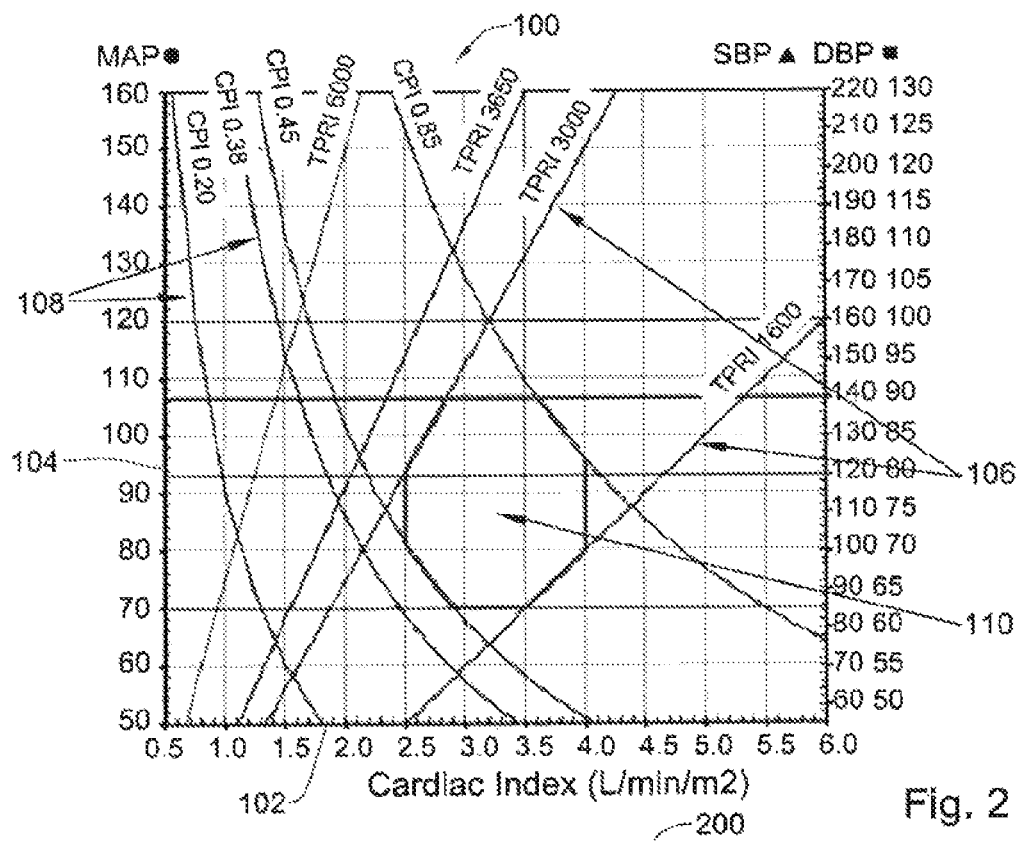
FIG. 2 illustrates a multi-dimensional graph of a Cardiovascular Status function with a normal safe zone according to the present invention.
FIG. 3 illustrates a multi-dimensional graph of a Cardiac Function with a normal safe zone according to the present invention.

The output data including the at least two multi-dimensional functions, the multi-parameter space, the individual medical parameters, and data indicative of the treatment plan is sent to an output device 50 which may be operated to present the data to a user. The output device may be a monitor, a speaker or other known platform suitable for presenting the data output from the processing utility 40 to a user to facilitate inspection. The output of the output device may be visual, audible or a combination thereof. The output may be static or dynamic, presented on-line or off-line after being recorded. Preferably, the output device is configured and operable to present the treatment plan data graphically, and also with respect to the normal/desired condition to be obtained/approached as a result of the treatment. An exemplary output from the processing utility 40 is a chart as shown in FIG. 2 or FIG. 3.

The system 10 may produce a plan for navigating an examined subject/object with given individual medical parameters from a starting position towards the normal zone defined by the values of parameters in the multi-parameter space. The plan may be executed automatically or manually by a user. In the automatic mode, the system may be connected to a suitable instrumentation for administering substances to the subject/object, e.g. drugs and medications to a treated subject. In medical scenario, a subject suffering from medical disorder having medical parameter values outside the safe zone should be treated and navigated into the safe zone. This will be further described below.

The system utilizes a predetermined degree of matching (predefined solutions) stored in the system to offer the navigation plan. The predefined solution may refer to navigation based on a single function (e.g. the Cardiovascular Status function) or a plurality of functions, such as the two functions: the Cardiovascular Status function and the Cardiac function, as will be further described below.

As mentioned earlier, the system is specifically directed towards emergency medicine, in which a patient is not balanced hemodynamically and needs to receive appropriate continuous monitoring and optionally suitable treatment that might involve several stages, in order to stabilize him. The system is configured for displaying the patient relevant hemodynamic individual parameters of specific function(s) (e.g. Cardiac function, SI vs. HR) on a map that also includes the safe zone for a balanced subject, giving online information to the physician to enable the physician to make decisions, and optionally calculating the distance and orientation of the individual parameters relative to the normal safe zone, i.e. a degree of matching, and generating a treatment plan accordingly based on the predefined solutions saved in the system. The treatment plan preferably includes as low as possible stages/sessions. After each treatment stage, the patient's individual medical parameters may be measured, acquired (e.g., calculated) and displayed instead of or in addition to the previous measured/calculated parameters, then another suitable treatment (updated treatment plan) is generated for the user's consideration. The system continues to receive measured data and generate treatment plans (updates) until the measured data indicate that the subject has entered the safe zone or satisfied the predetermined degree of matching between the safe zone and his medical condition (i.e. desired zone/conditions).

As described earlier, according to the invention the system and the method performed by the system (with or without interference from a user), utilize two hemodynamic functions simultaneously in order to give enough information about the patient's condition. In the following, description of exemplary embodiments for these two functions, and study cases utilizing the invention, are described.

FIG. 2 illustrates a multi-dimensional graph 100 of the Cardiovascular Status multi-dimensional function as defined in the present invention, with MAP, Systolic Blood Pressure (SBP), Diastolic Blood Pressure (DBP) at the y axis and CI at the x axis, together with lines/curves for TPRI and CPI plotted on the graph body. Specifically, the graph 100 shows CI having values in the range of 0.5-6.0 at the x axis 102; MAP, SBP and DBP having values in the range of 40-160, 40-220 and 40-130 respectively at the y axis 104. Also shown five lines 106 which indicate points on the graph 100 along which constant values of TPRI exist, these lines 106 have the constant values of 6000, 3650, 3000, 1600 and 1,350 for TPRI. Two of these lines, 3,000 and 1,600, are constant and represent normal (safe) zone while the lines 3,650 and 1,350 can be modified by the user to define a target zone for a specific subject. As noted and expected, the value of CI increases as TPRI decreases, also it can be seen that for a specific value of TPRI, MAP and CI are directly proportional. Curves 108 exemplify points on the graph 100 at which CPI has a constant value. Five declining curves are shown with CPI constant values 0.20, 0.38, 0.45, 0.85 and 1.00. Two of these lines, 0.45 and 0.85, are constant and represent normal range or safe zone; while the lines 0.38 and 1.00 can be modified by the user to define a target zone for a specific subject. It is clearly noted that for a constant value of CPI, as CI increases MAP decreases with an exponential relationship.

The graph also shows a normal (safe) zone 110 in which a balanced human being is usually found. The normal zone (region) 110 is a multi-parameter space that has well defined borders defined by values of MAP, CI, CPI and TPRI. The values of the borders were obtained statistically from a large number of healthy/balanced examined human subjects. As shown, the safe zone exists between 2.5-4.0 for CI, 70-105 for MAP, and is further confined by the values 3000-1600 for TPRI and 0.45-0.85 for CPI. A subject having medical parameters found outside the normal zone is not balanced/not safe and should be treated and brought into the normal zone by applying treatment/administering medication and navigating him from his starting position until he enters the safe zone, or be brought into a vicinity of the normal zone of the multi-parameter space. In the event that a different safe zone may be required for a specific subject, the user can define such zone.

The number of steps of navigation is preferably as low as possible, and may be performed manually by a physician, automatically by the navigating system or with both options, such that the physician can, at any stage during the treatment process, stop the automatic procedure and apply his manual input. The physician can also activate the system in such a way that every automatic step made by the system requires the physician approval beforehand.

Referring to FIG. 3, the Cardiac Function function as defined by the present invention is shown. A graph 200 relates the CI to HR at the x axis and the SI at the y axis. Specifically, the graph 200 shows HR having values in the range of 45-145 at the x axis 202, and SI having values in the range of 10-80 at the y axis 204. Also shown arc eleven curves 206 which indicate points on the graph 200 along which constant values of CI exist, these curves 206 have the constant values of 1.5-6.5 for CI with a 0.5 step between the adjacent curves. It can be seen that for a specific value of CI, as HR increases SI decreases with an exponential relationship.

The graph also shows a multi-parameter space forming a normal (safe) zone 210 in which a balanced human being is found. The normal zone (region) 210 has well defined borders defined by values of HR, SI and CI. The values of the borders were obtained statistically from a large number of healthy/balanced examined human subjects. As shown, the safe zone exists between 60-90 for HR, and 35-65 for SI, and it is further confined by the values 2.5-4.0 for CI. Every subject being outside the normal zone is not balanced/not safe and should be treated and brought into the normal zone, or at its vicinity by applying treatment/administering medication and navigating him from his starting position until a second position inside or adjacent the safe zone 210.

Figure 4:
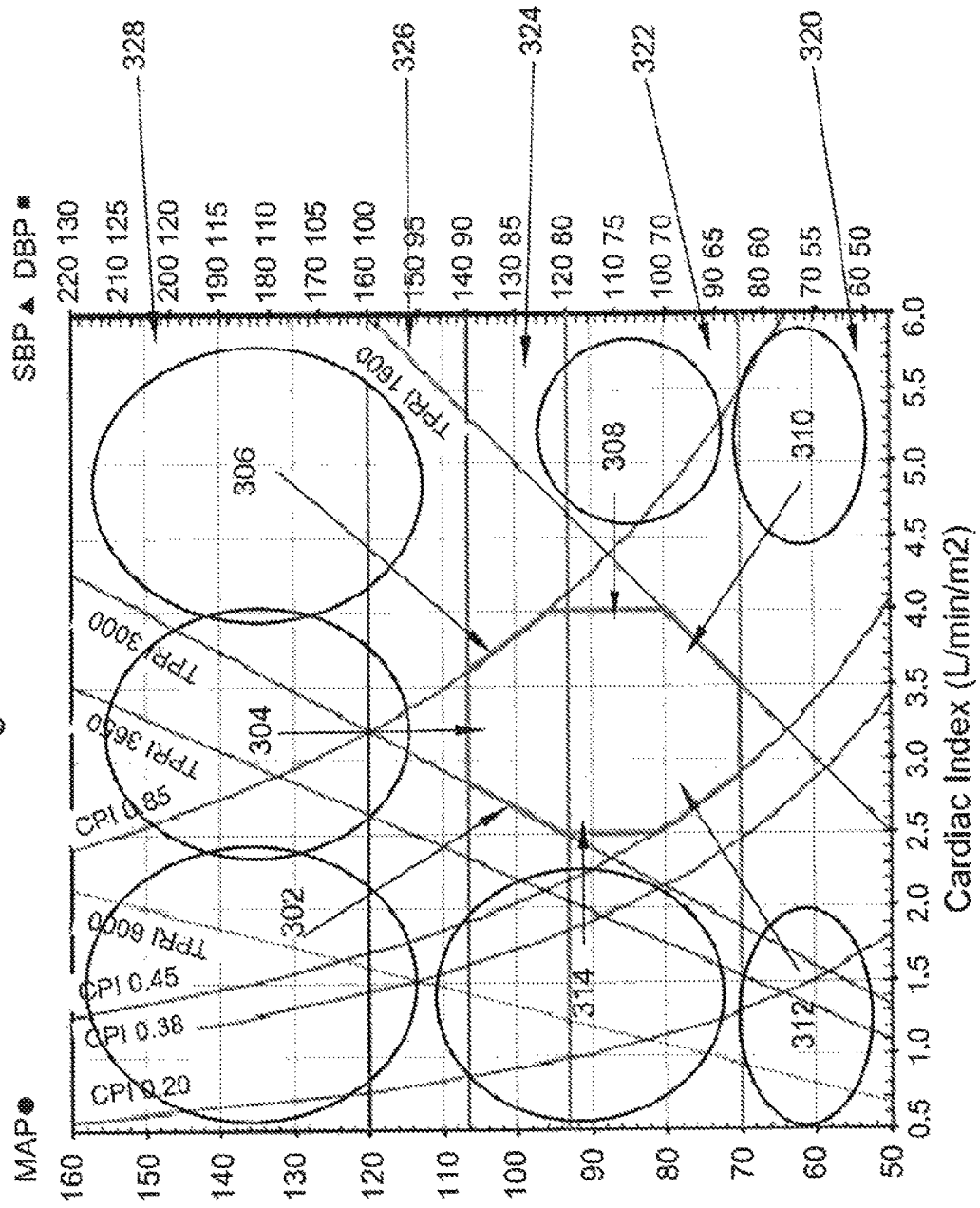
FIG. 4 illustrates different characteristics of regions in the Cardiovascular Status graph.

Referring to FIG. 4 which illustrates the Hemodynamic Status map, i.e. TPRI and CPI vs. CI, SBP, DBP and MAP, the graph mapping the Hemodynamic Status can be divided into five different regions along the y axis:

The region 320: MAP<70, is characterized by Hypotension (low pressure);

The region 322: 70<MAP<93, is the normal range;

The region 324: 120<SBP<140 or 80<DBP<90, is characterized by pre Hypertension (pre high pressure);

The region 326: 140<SBP<160 or 90<DBP<100, is characterized by stage 1 Hypertension;

The region 328: 160<SBP or 100<DBP, is characterized by stage 2 Hypertension.

When the CI information is taken into account, a more specific diagnosis is achieved. This is illustrated on the hemodynamic status map by the numbers 302-314 exemplifying states/conditions of patients suffering from disorder in their hemodynamic status and who should be treated in order to bring them to the normal safe zone, or the user predefined zone for a specific subject, as illustrated by the arrows on the graph.

A patient found at position (region, state) 302 (characterized by High TPRI. Low CI and High Blood Pressure) suffers from Vasoconstriction, i.e. a narrowing of the blood vessels resulting from contraction of the muscular wall of the vessels. This will restrict the blood flow and will increase the TPRI, resulting in increase of blood pressure and decrease of blood flow. A patient in this state is usually treated with adding/increasing dose of ACEI, ARB or other vasodilators and, if the patient is on Beta blockers, reducing Beta blockers, in order to reach TPRI<3,650 or other value as may be predefined by the user.

A patient at position 306 (characterized by Normal TPRI, High CI and High Blood Pressure) is Hyperdynamic (increased cardiac output resulting in high blood pressure). If the patient suffers from High SI, then increasing dose/adding CCB with Negative Inotropic Effect (e.g. Verapamil) should be considered, whereas if the patient suffers from High HR, then increasing dose/adding Beta blockers is required. The target of the treatment should be CPI<1.00 or other value as may be predefined by the user.

Position 304 (High Blood Pressure and Normal CI) indicates a patient with Mixed Hemodynamic, i.e. a combination of both vasoconstricted and hyperdynamic. In this case there is a need to consider increasing dose/adding ACEI, ARB or other Vasodilator; also increasing/adding CCB, Beta blockers or Negative Inotropic Agents. Position 308 (Low TPRI, Normal Blood Pressure and High CI) describes a patient having High Cardiac Output Failure. This could be caused by various causes that should be identified and treated. These causes include increased blood volume, e.g. from excess of water and salt (renal pathology, excess of fluid or blood administration, treatment with retaining water steroids), chronic and severe anemia, large arteriovenous fistula or multiple small arteriovenous shunts, some forms of severe hepatic or renal disorders, hyperthyroidism, and wet beriberi. The cause should be identified and treated. The target is TPRI<1,350 and CPI<1.0 or other values as may be predefined by the user.

Position 310 (Low TPRI, High CI, Normal CPI and Low Blood Pressure) indicates that the patient suffers from Distributive Shock, meaning abnormal distribution of blood flow in the smallest blood vessels which results in inadequate supply of blood to the body's tissues and organs. It is one of four categories of shock, a condition where there is not enough oxygen-carrying blood to meet the metabolic needs of the cells. Distributive shock is different from the other three categories of shock in that it occurs even though the output of the heart is at or above a normal level. This could be caused by various causes that should be identified and treated. These causes include septic shock, anaphylactic shock, adrenal insufficiency, neurogenic shock. The target is TPRI>1,350 or other value as may be predefined by the user.

A patient at position 312 (Low TPRI and Low CPI) suffers from Cardiogenic Shock, i.e. sustained hypotension with tissue hypoperfusion despite adequate left ventricular filling pressure. Signs of tissue hypoperfusion include oliguria (<30 mL/h), cool extremities, and altered level of consciousness. Positive Inotropic Agent (e.g. Cardiac Glycoside) should be increased/added. In the event of high HR, dose of Beta blocker should be increased/added. Some medications to be considered are Aldospirone and Digoxin. Treatment should aim to CPI>0.38 and MAP>65 or other values as may be predefined by the user.

Position 314 (High TPRI, Low CPI, Low CI and Normal Blood Pressure) describes a patient suffering from Congestive Heart Failure, i.e. inability of the heart to pump sufficiently to maintain blood flow to meet the needs of the body. In this situation, consideration should be made whether to increase dose/add ACEI, ARB, and if not effective add Hydralazin. Consideration should be made whether to increase dose/add Positive Inotropic Agents. Consideration should also be made whether to give Aldospirone. The patient's state should be brought to CPI>0.38, TPRI<3,650 or other values as may be predefined by the user.

Figure 5:
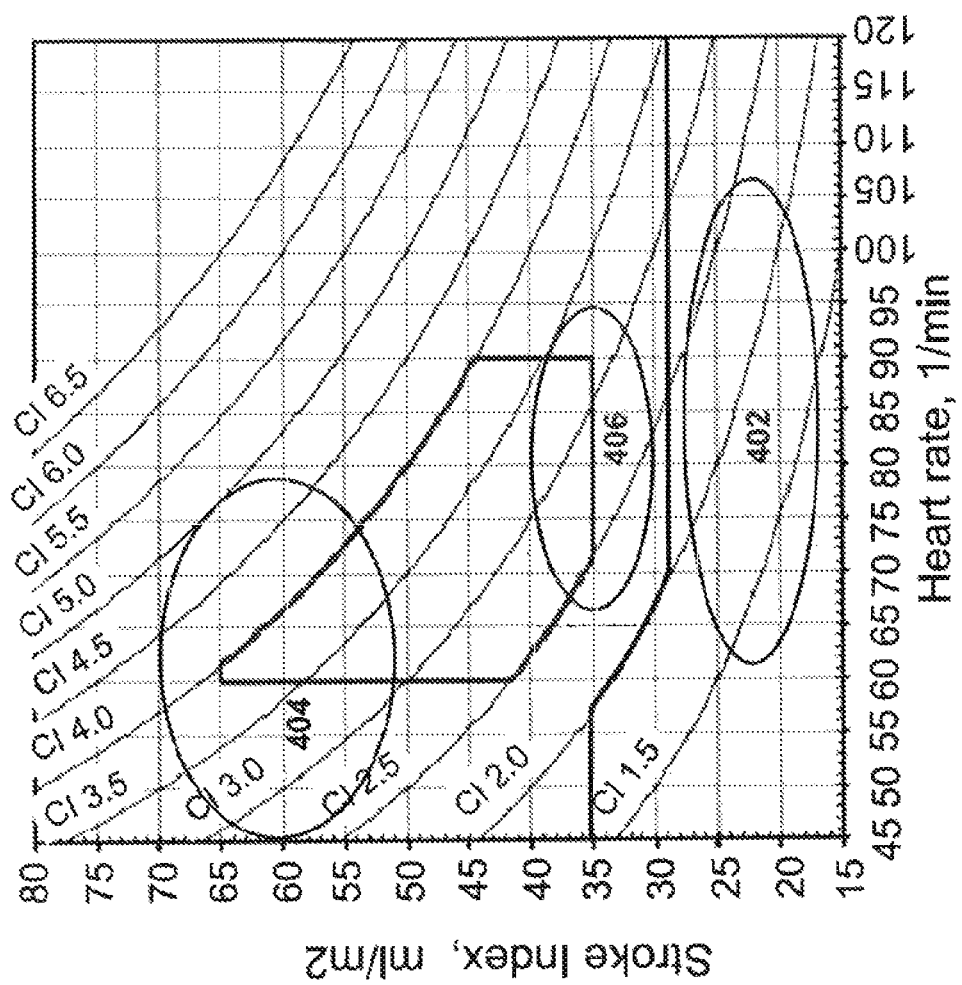
FIG. 5 illustrates different characteristics of regions in the Cardiac Function graph.

FIG. 5 illustrates subject conditions in regions (positions) 402, 404 and 406 on the Cardiac Function graph, which represent more hemodynamic states of subjects.

Condition (position) 402 represents a subject who suffers from Heart Failure (the same as condition 314), being located at the middle bottom part of the graph and represents SI<29 at wide range on HR.

Position 404 represents a subject characterized by High Cardiac Reserve, which means that CI is produced by low HR and high SI, hence the heart is potentially capable to substantially increasing CI.

Position 406 represents a subject characterized by Low Cardiac Reserve, which means that CI is produced by medium to high HR and low SI, hence the ability of the heart to increase CI is limited.

FIGS. 6-9 illustrate examples of using the invention in three case studies, showing how the graphs of the two multi-dimensional functions of Cardiovascular Status and Cardiac Function, forming one embodiment according to the invention, are essential in diagnosing the subject medical condition, and how they enable an effective treatment plan with as little as possible navigating stages.

Figure 6:
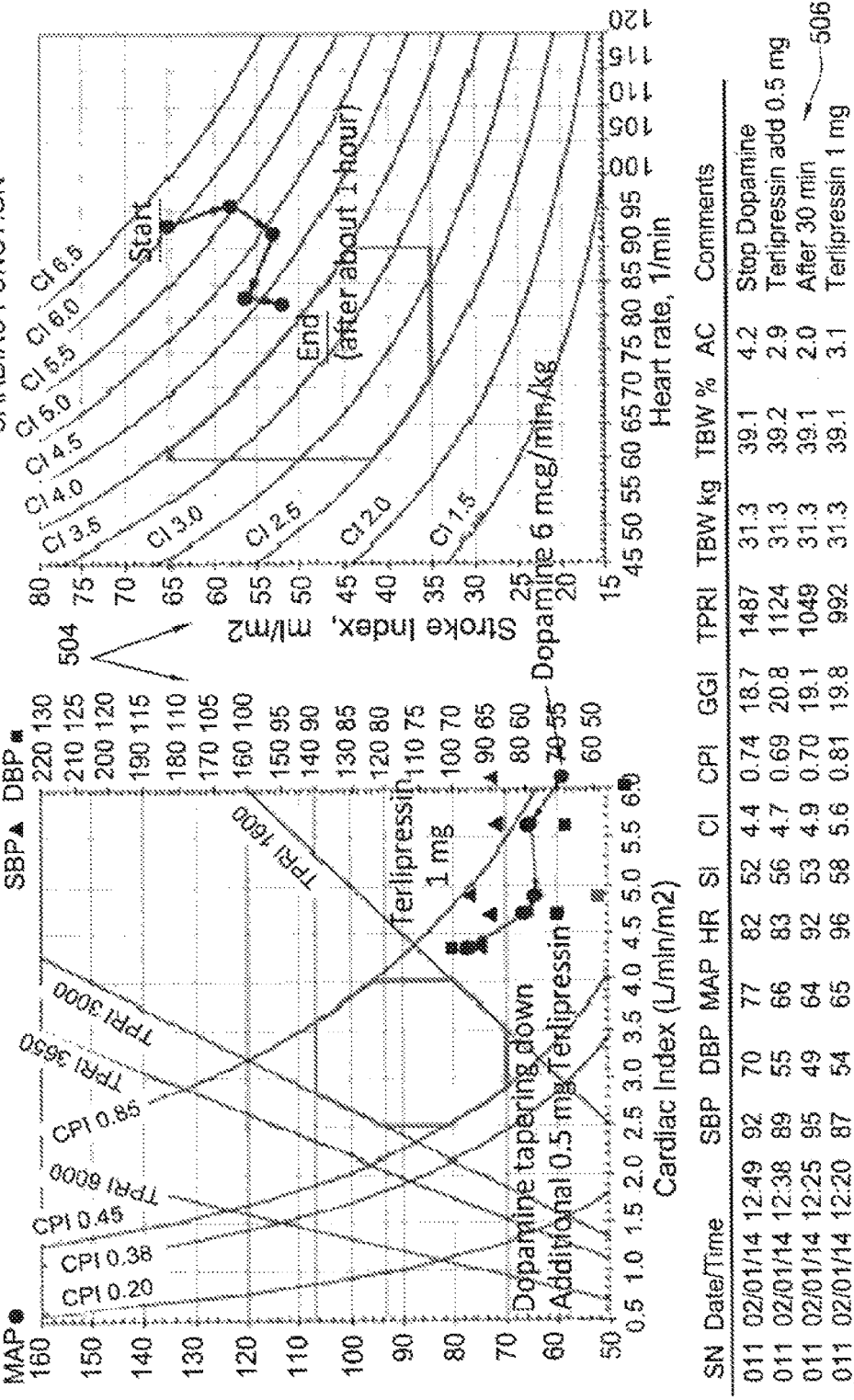
FIGS. 6 to 9 exemplify navigation of a subject from a first status to a second status according to embodiments of the present invention.

The first Case Study is shown in FIG. 6. The figure shows one exemplary user interface to be used with a system according to the invention. In the upper part 502, several personal data, such as name height weight BSA and age can be displayed; they can be entered by a user, received from direct measurements, or imported from a database. In the lower part 506 of the interface, a table summarizes the medical data and/or the individual hemodynamic parameters that are measured or calculated, the times of the measurements, and a comments column that may include the instructions of the treatment plan, such as names of medications administered. The major part of the interface at the center 504 is dedicated to the graphs that the user is interested in plotting, e.g. the cardiovascular status and the cardiac function. Every measurement is pointed on the graphs and an arrow may connect between each point and the subsequent point to provide traction of the progress. In this case, a 44 years old female arrived to Intensive Care Unit (ICU) after suicide attempt with Calcium Channel Blocker (CCB) and Angiotensin Converting Enzyme Inhibitor (ACEI). She arrived with hypotension (blood pressure of 88/44), low HR of 53, oliguria and acute renal failure. The patient was alerted with warm and dry skin. Due to the low blood pressure and the presumption that the CCB implicated negative inotropic effect, she was commenced on fluids and Dopamine at a dose of 5 mcg/kg/min in order to elicit a positive inotropic effect. However, after connecting her to the system of the invention, the graphic display immediately pointed to zone 310 in the Cardiovascular status graph (FIG. 4) which implicates very high CI and very low TPRI which should imply the possibility of Distributive Shock to abnormal vasodilation mediated by CCB. The patient was treated with pure vasoconstrictor (Glypressin) in replace of the Dopamine. As a result, the TPR increased, CI reduced, and blood pressure increased so that target BP, has been met by manipulating the TPR condition while controlling the SV and CI. The navigation of the patient from a dangerous state to a stable one lasted for about one hour during which her individual hemodynamic parameters were monitored by the system several times. The navigation of the patient through the stages can be performed fully automatically by the system 10, fully manually by the practitioner, or in a semi-automatic fashion, for example the system generates a new treatment plan after each measurement of the individual hemodynamic parameters, carried out manually or periodically at fixed predetermined time intervals, and waits for the practitioner/operator to confirm the treatment plan. It should be understood that the technique of the invention advantageously provides for producing an image that immediately hints the users as to the nature of the hemodynamic problem.

Figure 7:
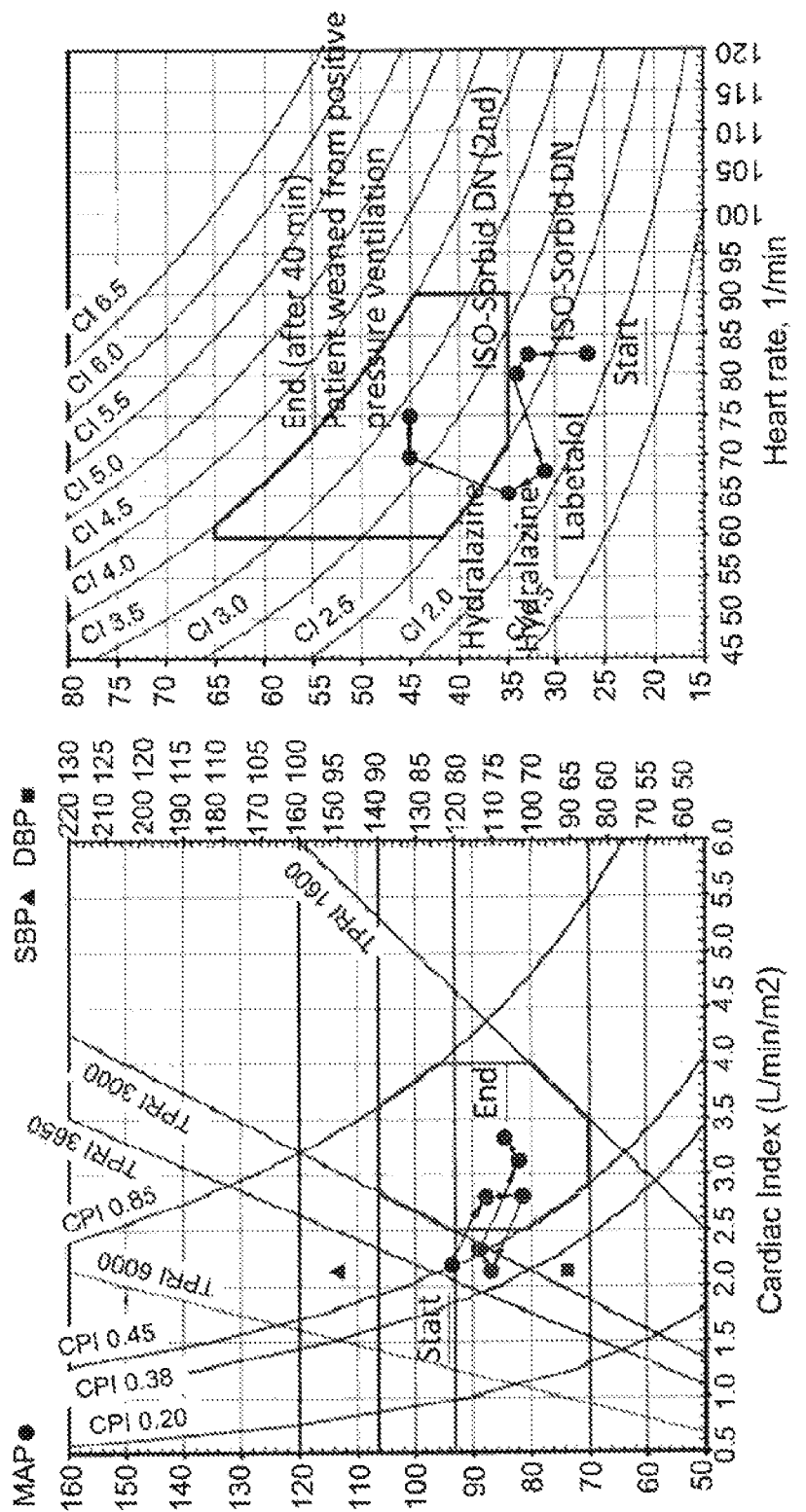

FIG. 7 shows the second Case Study of a 71 years old male with severe shortness of breath and in need for positive pressure mechanical ventilation. Past medical history revealed acute heart failure due to severe left ventricular systolic dysfunction. The system of the invention reveals the patient to be in Zone 402 of the Cardiac Function (FIG. 5) and zone 314 of the Cardiovascular status (FIG. 4). These zones imply a low SI, low CI and high TPRI of 3,600. Various medications were titrated until Hydralazine was found to be the most effective once. Within about 40 min patient's hemodynamic parameters were optimized into the normal range. The main advantage of the graphic display in this patient was in helping the user to understand immediately the nature of the hemodynamic compromise and afterwards to get an impression of the patient progressing overtime. The system allows the users to be aware of hemodynamic changes taken place in many variables during the treatment time. The patient felt better and was weaned from positive pressure ventilation. The treatment included seven measurements of the individual hemodynamic parameters and six treatment stages.

Figure 8:
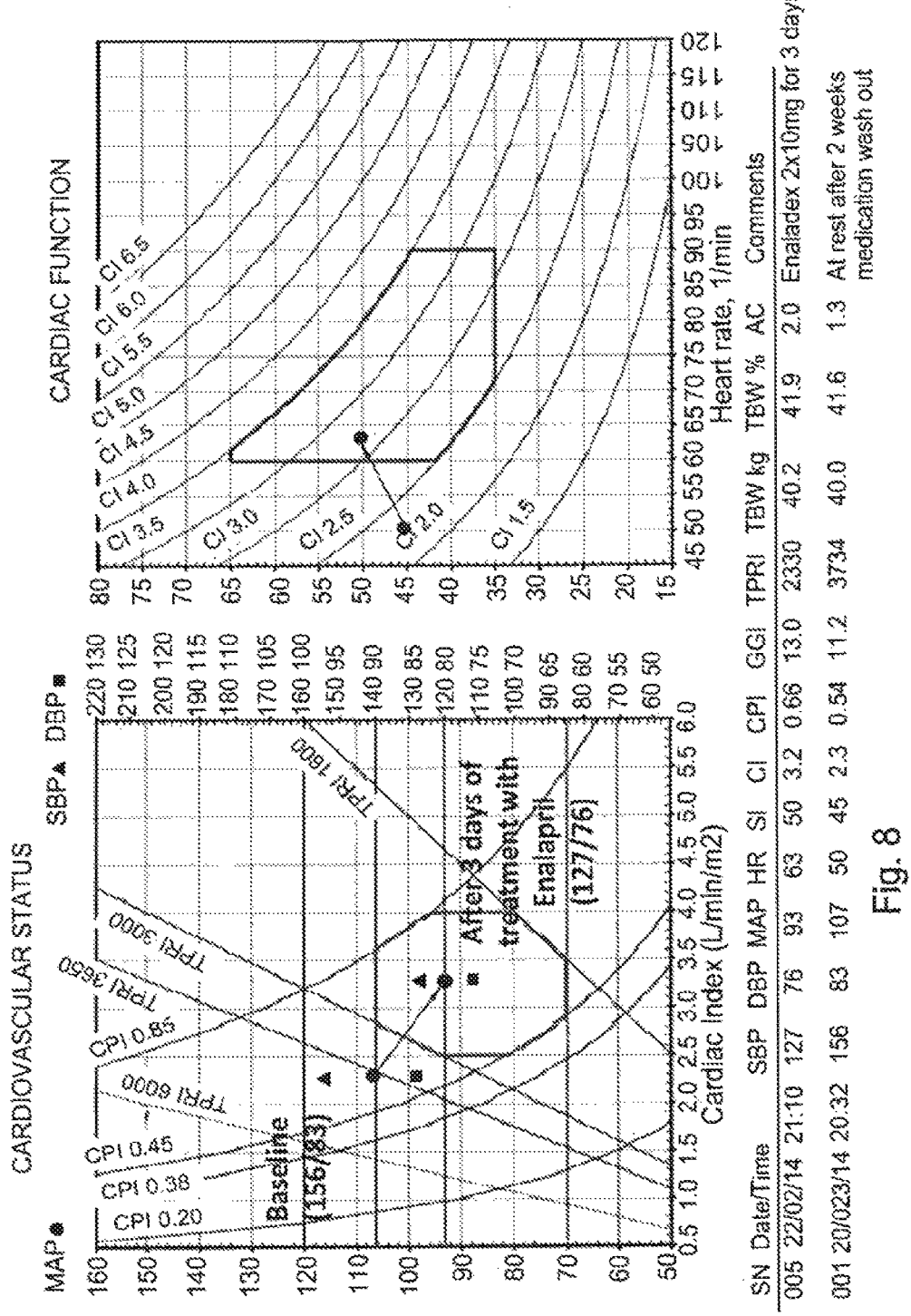

The case study of a 50 years old male with long history of hypertension is shown in FIG. 8. The patient was treated with Vasrodip Combo (Lercanidipine 10 mg+Enalapril 20 mg). The patient complained for weakness, sleepiness and difficulty to perform physical efforts which he attributed to his medications. The patient decided to stop drug treatment 2 weeks prior to measurement carried out by the system of the invention. By performing the measurement it was found that the patient is in zone/condition which implicates vasoconstricted hemodynamic with high blood pressure. The conclusion was that the patient was treated by the correct medications. The patient was then re-treated by Enalapril. After 3 days, the patient's hemodynamic state was optimized into the normal range.

Figure 9:
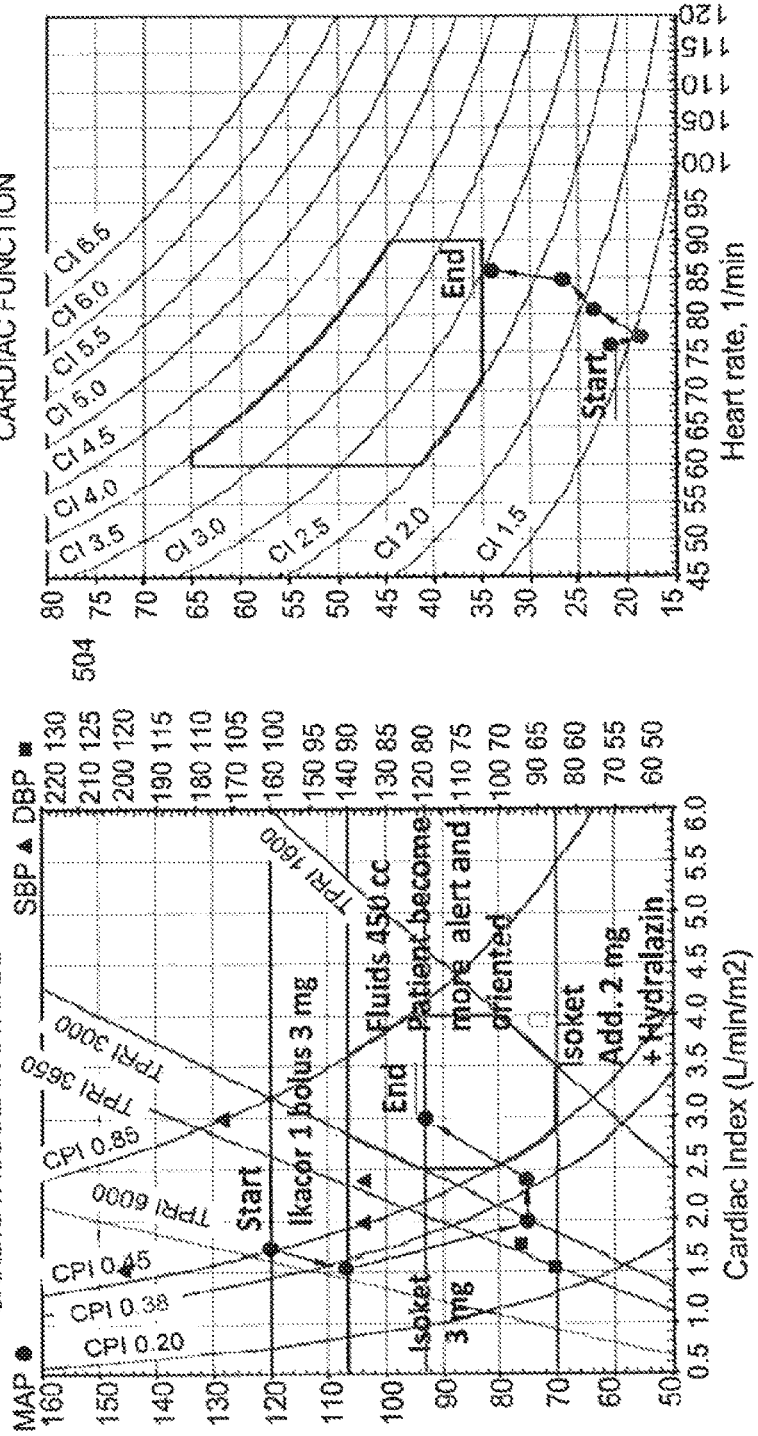

FIG. 9 illustrates the ability of the system to detect wrong treatment decisions. In this case, a 79 year old patient is examined, who has been treated in the ICU for post operative complications among which acute lung injury was treated with oxygen therapy and diuretics. He has also been under medical investigation for lethargy and confusion. The patient was examined by the technique of the invention because of uncontrolled hypertension in the ICU. The first measurement found the patient to be in zone 402 of the Cardiac Function (FIG. 5) and zone 302 of the Cardiovascular status (FIG. 4), which indicates low CI and high TPR conditions. The physicians in charge decided to treat the patient with iso-sorbid di nitrate which is aimed at lowering the patient blood pressure by veno and arterial dilation. The re-measurement of the patient after this treatment clearly shows on the graphic display that although the blood pressure dropped, the direction of hemodynamic status has moved away from the desired safe zone. The treatment that eventually improved the patient's hemodynamic condition was administration of fluids. The patient not only improved hemodynamically but improved his mental state and become more alert and attentive. Analyzing the case shows that the system helped in recognizing and identifying wrong medical decision (which would otherwise be not timely identified) and is helpful to users in displaying complex integrative trends.

The invention claimed is:

1. A computerized system for use in monitoring a hemodynamic condition of a subject, the system comprising:
    a data input utility configured and operable for receiving medical data of the subject, the data being indicative of a first hemodynamic condition of the subject;
    a communication utility configured and operable for accessing a database for obtaining therefrom reference data comprising at least two predefined multi-dimensional functions of medical parameters and respective multi-parameter spaces within said at least two multi-dimensional functions, each multi-parameter space corresponding to a normal condition of the subject within the respective multi-dimensional function, and each multi-parameter space having well defined boundaries defined by values of all the parameters within the respective multi-dimensional function; and
    a processing utility connected to the data input utility and to the communication utility, said processing utility being preprogrammed for processing said medical data of the subject utilizing said at least two predefined multi-dimensional functions, said processing comprising:
        a parameter identifier configured and operable for identifying in said medical data a plurality of individual medical parameters describing said at least two predefined multi-dimensional functions, an analyzer configured and operable for analyzing, for each of the multi-dimensional functions, the identified plurality of individual medical parameters and determining a relation between the plurality of individual medical parameters and the respective multi-parameter space, and utilizing said relation for determining a treatment plan of one or more treatment steps, wherein the determining is performed by selecting from predefined solutions that tell for said relation what treatment step(s) should be performed for navigating the subject from said first condition to a second hemodynamic condition of the subject in which values of said plurality of medical parameters define respective parametric spaces matching the multi-parameter spaces of the normal condition according to predetermined degrees of match in each multi-dimensional function, and an output utility for generating output visual data indicative of said at least two multi-dimensional functions, said respective multi-parameter spaces, and said one or more treatment steps of the treatment plan.

2. The system of claim 1, wherein said output utility is configured and operable for a simultaneous display of said at least two multi-dimensional functions and said plurality of individual medical parameters within said multi-dimensional functions, thereby displaying said relation between the first condition of the subject and the second condition of the subject.

3. The system of claim 2, wherein said output utility is configured for formatting the output data for said simultaneous display in graphical fashion.

4. The system according to claim 1, wherein said medical data of a subject comprises at least two of: a Heart Rate (HR), a Systolic Blood Pressure (SBP), a Diastolic Blood Pressure (DBP), a Body Surface Area (BSA), a Stroke Volume (SV), and a Mean Arterial Pressure (MAP).

5. The system according to claim 4, wherein said plurality of identified parameters comprise at least two of: a Total Peripheral Resistance Index (TPRI), a Cardiac Power Index (CPI), a Cardiac Output (CO), a Cardiac Index (CI), and a Stroke Index (SI).

6. The system according to claim 5, wherein said at least two predefined multi-dimensional functions comprise:
a multi-dimensional function of the MAP, the SBP and the DBP versus the CI, the TPRI and the CPI as functions of the MAP and the CI, describing a cardiovascular status of the subject;
a multi-dimensional function of the SI versus the HR, and the CI as a function of the SI and the HR, describing a cardiac function of the subject.

7. The system according to claim 6, wherein said multi-parameter spaces of the normal condition are defined by the following normal parameter values: $70<MAP<105$, $2.5<CI<4.0$, $0.45<CPI<0.85$, $1600<TPRI<3000$, $35<SI<65$, and $60<HR<90$.

8. The system according to claim 1, wherein said identifier utility is configured for using the medical data and calculating therefrom at least some of said plurality of the parameters describing said at least two predefined multi-dimensional functions.

9. The system according to claim 1, wherein said processor utility is configured and operable for automatically generating instructions for implementation of the treatment plan.

10. The system according to claim 1, being configured for receiving a user input and generating instructions for implementation of the treatment plan based on the user input.

11. The system according to claim 1, further comprising a memory utility for storing the medical data of the subject and the identified parameter values, and the multi-parameter spaces of the normal condition.

12. The system according to claim 1, wherein said processor utility is further configured and operable for updating the multi-parameter spaces of the normal condition based on said medical data of the subject.

13. A computerized method for use in monitoring a hemodynamic condition of a subject, the method comprising:
operating a data input utility of a computer for receiving medical data indicative of a first hemodynamic condition of the subject;
accessing a database for obtaining therefrom reference data comprising at least two predefined multi-dimensional functions of medical parameters and respective multi-parameter spaces within said at least two multi-dimensional functions, each multi-parameter space corresponding to a normal condition of the subject within the respective multi-dimensional function, and each multi-parameter space having well defined boundaries defined by values of all the parameters within the respective multi-dimensional function; and
processing and analyzing the medical data utilizing said at least two predefined multi-dimensional functions, said processing and analyzing comprising: identifying in said medical data a plurality of individual medical parameters describing said at least two predefined multi-dimensional functions, analyzing for each of the multi-dimensional functions the identified plurality of individual medical parameters, and determining a relation between the plurality of individual medical parameters and the respective multi-parameter space, and utilizing said relation for determining a treatment plan of one or more treatment steps, wherein the determining is performed by selecting from predefined solutions that tell for said relation what treatment step(s) should be performed for navigating the subject from said first condition to a second hemodynamic condition of the subject in which values of said plurality of individual medical parameters define respective parametric spaces matching the multi-parameter spaces of the normal condition according to predetermined degrees of match in each multi-dimensional function, and generating output visual data indicative of said at least two multi-dimensional functions, said respective multi-parameter spaces and said one or more treatment steps of the treatment plan.

14. The method of claim 13, comprising simultaneously displaying said at least two multi-dimensional functions and said plurality of individual medical parameters within said multi-dimensional functions, thereby displaying said relation between the first condition of the subject and the second condition of the subject.

15. The method of claim 14, wherein said simultaneous display comprises a graphical presentation.

16. The method according to claim 13, wherein said medical data of a subject comprises at least two of: a Heart Rate (HR), a Systolic Blood Pressure (SBP), a Diastolic Blood Pressure (DBP), a Body Surface Area (BSA), a Stroke Volume (SV), and a Mean Arterial Pressure (MAP).

17. The method according to claim 16, wherein said plurality of identified parameters comprise at least two of: a Total Peripheral Resistance Index (TPRI), a Cardiac Power Index (CPI), a Cardiac Output (CO), a Cardiac Index (CI), and a Stroke Index (SI).

18. The method according to claim 17, wherein said at least two predefined multi-dimensional functions comprise:
- a multi-dimensional function of the MAP, the SBP and the DBP versus the CI, the TPRI, and the CPI as functions of the MAP and the CI, describing a cardiovascular status of the subject;
- a multi-dimensional function of the SI versus the HR, and the CI as a function of the SI and the HR, describing a cardiac function of the subject.

19. The method according to claim 18, wherein said multi-parameter spaces of the normal condition are defined by the following normal parameter values: 70<MAP<105, 2.5<CI<4.0, 0.45<CPI<0.85, 1600<TPRI<3000, 35<SI<65, and 60<HR<90.

20. The method according to claim 13, comprising using the medical data and calculating therefrom at least some of said plurality of the parameters describing said at least two predefined multi-dimensional functions.

21. The method according to claim 13, wherein said processing and analyzing comprises automatically generating instructions for implementation of the treatment plan.

22. The method according to claim 13, comprising receiving a user input and generating instructions for implementation of the treatment plan based on the user input.

23. The method according to claim 13, further comprising storing the medical data of the subject and the identified parameter values, and the multi-parameter spaces of the normal condition.

24. The method according to claim 13, wherein said processing and analyzing further comprises generating update data for updating the multi-parameter spaces of the normal condition based on said medical data of the subject.

* * * * *